(12) United States Patent
Li et al.

(10) Patent No.: US 11,256,891 B2
(45) Date of Patent: Feb. 22, 2022

(54) ARRAY SUBSTRATE, METHOD OF MANUFACTURING ARRAY SUBSTRATE, AND DISPLAY APPARATUS

(71) Applicant: BOE Technology Group Co., Ltd., Beijing (CN)

(72) Inventors: Haixu Li, Beijing (CN); Zhanfeng Cao, Beijing (CN); Jianguo Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 316 days.

(21) Appl. No.: 16/607,192

(22) PCT Filed: May 8, 2019

(86) PCT No.: PCT/CN2019/085973
§ 371 (c)(1),
(2) Date: Oct. 22, 2019

(87) PCT Pub. No.: WO2020/015440
PCT Pub. Date: Jan. 23, 2020

(65) Prior Publication Data
US 2020/0242324 A1 Jul. 30, 2020

(30) Foreign Application Priority Data
Jul. 20, 2018 (CN) .......................... 201810803078.5

(51) Int. Cl.
*G06K 9/00* (2006.01)
*H01L 27/32* (2006.01)
*G02F 1/1368* (2006.01)

(52) U.S. Cl.
CPC ...... *G06K 9/00013* (2013.01); *H01L 27/3234* (2013.01); *G02F 1/1368* (2013.01)

(58) Field of Classification Search
CPC ........ A61B 2562/0233; A61B 2562/12; A61B 5/1172; G02F 1/13312; G02F 1/1368;
(Continued)

(56) References Cited

U.S. PATENT DOCUMENTS 9,293,517 B2  3/2016  Li et al.
10,489,628 B2  11/2019  Liu et al.
(Continued)

FOREIGN PATENT DOCUMENTS

CN  104035253 A  9/2014
CN  106129069 A  11/2016

OTHER PUBLICATIONS

First Office Action, including search report, for Chinese Patent Application No. 201810803078.5, dated Aug. 17, 2021, 13 pages.

*Primary Examiner* — Michael J Vanchy, Jr.
(74) *Attorney, Agent, or Firm* — Westman, Champlin & Koehler, P.A.; Judson K. Champlin

(57) ABSTRACT

An array substrate, a method of manufacturing the array substrate, and a display apparatus are disclosed. The array substrate includes: a base substrate; a plurality of sensing elements disposed on a first side of the base substrate and each configured to convert at least one of a light signal and an acoustic wave signal into an electrical signal; and a plurality of switching devices disposed on a second side of the base substrate opposite to the first side. The plurality of switching devices include a plurality of first switching elements, and each of the plurality of first switching elements is electrically connected to a corresponding one of the plurality of sensing elements to transmit the electrical signal.

20 Claims, 4 Drawing Sheets

(58) Field of Classification Search
CPC .............. G06K 9/00013; G06K 9/0002; H01L 27/3234; H04R 1/08; H04R 1/342; H04R 29/004
See application file for complete search history.

(56) References Cited

U.S. PATENT DOCUMENTS

| | | | |
|---|---|---|---|
| 2015/0340419 A1 | 11/2015 | Li et al. | |
| 2016/0132713 A1 | 5/2016 | Bae et al. | |
| 2017/0351364 A1* | 12/2017 | Kim | ...................... G06F 3/0412 |
| 2018/0285617 A1 | 10/2018 | Liu et al. | |
| 2019/0197282 A1* | 6/2019 | Gong | ...................... G06F 1/182 |

* cited by examiner

ARRAY SUBSTRATE, METHOD OF MANUFACTURING ARRAY SUBSTRATE, AND DISPLAY APPARATUS

CROSS-REFERENCE TO RELATED APPLICATION

This application is a Section 371 National Stage Application of International Application No. PCT/CN2019/085973, filed on May 8, 2019, entitled "ARRAY SUBSTRATE, METHOD OF MANUFACTURING ARRAY SUBSTRATE, AND DISPLAY APPARATUS", which has not yet published, which claims priority to Chinese Application No. 201810803078.5, filed on Jul. 20, 2018, incorporated herein by reference in their entireties.

TECHNICAL FIELD

Embodiments of the present disclosure relate to an array substrate, a method of manufacturing the array substrate, and a display apparatus.

BACKGROUND

A display apparatus such as a liquid crystal display or an electroluminescent organic light-emitting diode display typically has a fingerprint identification function.

SUMMARY

Embodiments of the present disclosure provide an array substrate, a method of manufacturing the array substrate, and a display apparatus including the array substrate. The array substrate includes: a base substrate; a plurality of sensing elements disposed on a first side of the base substrate and each configured to convert at least one of a light signal and an acoustic wave signal into an electrical signal; and a plurality of switching devices disposed on a second side of the base substrate opposite to the first side. The plurality of switching devices include a plurality of first switching elements, and each of the plurality of first switching elements is electrically connected to a corresponding one of the plurality of sensing elements to transmit the electrical signal.

In some embodiments, each of the plurality of sensing elements includes a first electrode electrically connected to a corresponding one of the plurality of first switching elements, a second electrode configured to receive a reference electric potential, and a sensing layer disposed between the first electrode and the second electrode.

In some embodiments, the sensing layer includes a light sensitive material or a sound sensitive material.

In some embodiments, the base substrate includes a plurality of via holes, the first electrode of each of the plurality of sensing elements is electrically connected to the corresponding one of the plurality of first switching elements through a corresponding one of the plurality of via holes, and a diameter of each of the plurality of via holes and a spacing between two adjacent ones of the plurality of via holes each are not greater than an interline spacing of a fingerprint of a finger.

In some embodiments, the array substrate includes a display area, and the display area includes: a first region within which the plurality of sensing elements and the plurality of first switching elements are located; and a second region around the first region.

In some embodiments, the plurality of switching devices further include second switching elements located in the second region, and the plurality of first switching elements and the second switching elements each include a thin film transistor, and the first electrode of each of the plurality of sensing elements is electrically connected to a source electrode or a drain electrode of one of the plurality of first switching elements. A gate electrode of each of the plurality of first switching elements and the second switching elements is configured to receive a first control signal to drive a pixel in the display area in a first period of time, and the gate electrode of each of the plurality of first switching elements is further configured to receive a second control signal to transmit the electrical signal in a second period of time.

In some embodiments, the array substrate further includes a metal lead electrically connected to the first electrodes of the plurality of sensing elements and configured to be electrically connected to an energy storage element that is independent of the array substrate.

In some embodiments, the array substrate further includes electroluminescent organic light-emitting elements located on the second side of the base substrate and electrically connected to the plurality of switching devices, respectively, and an orthogonal projection of each of the sensing layers on the base substrate does not overlap an orthogonal projection of a non-transparent region of a corresponding one of the first switching elements on the base substrate and an orthogonal projection of a non-transparent region of a corresponding one of the electroluminescent organic light-emitting elements on the base substrate.

In some embodiments, an orthogonal projection of each of the sensing layers on the base substrate coincides at least partly with an orthogonal projection of a corresponding one of the plurality of first switching elements on the base substrate.

In some embodiments, each of the plurality of sensing elements includes a dielectric layer covering the first electrode, the second electrode, and the sensing layer of the each of the plurality of sensing elements.

In some embodiments, the array substrate further includes a metal lead electrically connected to the first electrodes of the plurality of sensing elements, the sensing layers each include a light sensitive material and are configured to convert a received light into an electrical signal in a state where the sensing elements do not identify a fingerprint, and the metal lead is configured to be electrically connected to an energy storage element that is independent of the array substrate, so that the electrical signal is transmitted to the energy storage element.

Another embodiment of the present disclosure provides a display apparatus including the array substrate of any one of the above embodiments.

In some embodiments, each of the plurality of sensing elements includes an acoustic sensor configured to convert the acoustic wave signal into the electrical signal, and the display apparatus further includes an acoustic wave generator configured to generate an acoustic wave.

In some embodiments, the display apparatus further includes a rechargeable battery, and the plurality of sensing elements are further electrically connected to the rechargeable battery.

In some embodiments, the display apparatus further includes a rechargeable battery, the array substrate further includes a metal lead electrically connected to the first electrodes of the plurality of sensing elements, the sensing layers each include a light sensitive material and are configured to convert a received light into an electrical signal in a state where the sensing elements do not identify a fingerprint, and the metal lead is configured to be electrically connected to the rechargeable battery, so that the electrical signal is transmitted to the rechargeable battery.

A further embodiment of the present disclosure provides a method of manufacturing an array substrate, the method including: providing a base substrate; forming, on a first side of the base substrate, a plurality of sensing elements each configured to convert at least one of a light signal and an acoustic wave signal into an electrical signal; and forming a plurality of switching devices on a second side of the base substrate opposite to the first side, wherein the plurality of switching devices include a plurality of first switching elements, and each of the plurality of first switching elements is electrically connected to a corresponding one of the plurality of sensing elements to transmit the electrical signal.

In some embodiments, each of the plurality of sensing elements includes a first electrode, a second electrode, and a sensing layer located between the first electrode and the second electrode, and the method further includes: forming a plurality of via holes in the base substrate, wherein the first electrode of each of the plurality of sensing elements is electrically connected to a corresponding one of the plurality of first switching elements through a corresponding one of the plurality of via holes.

In some embodiments, the method further includes: forming a dielectric layer on a first side of the base substrate, wherein the dielectric layer covers the first electrodes, the second electrodes, and the sensing layers of the plurality of sensing elements.

In some embodiments, the array substrate includes a display area, and the display area includes: a first region within which the plurality of sensing elements and the plurality of first switching elements are located; and a second region around the first region.

In some embodiments, the plurality of switching devices further include second switching elements located in the second region, and the plurality of first switching elements and the second switching elements each include a thin film transistor, and wherein the first electrode of each of the plurality of sensing elements is electrically connected to a source electrode or a drain electrode of a corresponding one of the plurality of first switching elements, and a gate electrode of each of the plurality of first switching elements and the second switching elements is configured to receive a first control signal to drive a pixel in the display area in a first period of time, and the gate electrode of each of the plurality of first switching elements is further configured to receive a second control signal to transmit the electrical signal in a second period of time.

BRIEF DESCRIPTION OF THE DRAWINGS

In order to describe technical solutions according to embodiments of the present disclosure more clearly, accompanying drawings required for describing the embodiments will be simply explained as below. The accompanying drawings relate to only some of the embodiments of the present disclosure and should not be construed as limiting the protection scope of the present application.

DETAILED DESCRIPTION

Figure 1:
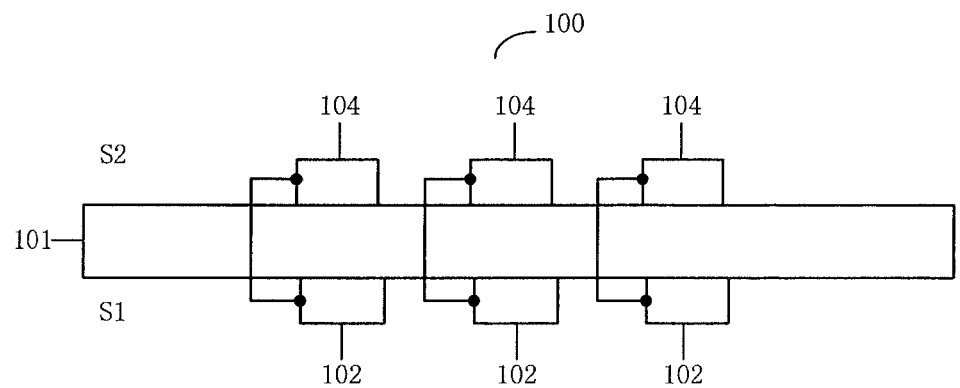
FIG. 1 is a block diagram schematically showing a structure of a portion of an array substrate according to an embodiment of the present disclosure.

In order that the objects, technical solutions, and advantages of embodiments of the present disclosure become more apparent, a clear and complete description of the technical solutions in the embodiments will be made as below in conjunction with the accompanying drawings. Apparently, the described embodiments are some of the embodiments of the present disclosure rather than all of the embodiments of the present disclosure. All other embodiments derived by those skilled in the art based on the described embodiments without making a creative work shall fall within the protection scope of the present disclosure.

Unless otherwise defined, technical or scientific terms used in the present disclosure should have the same meaning as commonly understood by one of ordinary skill in the art to which the present disclosure pertains. The terms "first" and "second" and similar words and phrases used in the present disclosure are used for only distinguishing different components from one another rather than indicating any sequence, number or importance. Likewise, the term "a", "an" or "the" or a similar word or phrase does not mean a limitation in number either, but denotes that there is at least one. The term "comprises", "comprising", "includes", "including" or any other similar word or phrase is to be construed to specify that an element or thing that appears before the term covers an element or thing that appears after the term and is listed and its equivalent, but do not exclude other elements or things. The term "connected" or any other similar word or phrase is not limited to a physical or mechanical connection but may include an electrical connection, regardless of a direct connection or an indirect connection. The terms "upper", "lower", "left", "right" and the like are only used to indicate relative positional relationships, and when an absolute position of the object being described is changed, the relative positional relationships may also change accordingly.

A fingerprint can be identified based on the uniqueness and stability of each person's fingerprint characteristic. For example, a user's true identity can be verified by comparing the user's fingerprint acquired on site with a prestored fingerprint. A light-sensitive sensing element is typically used in a fingerprint recognition technique. The light-sensitive sensing element can receive a light reflected by a user's finger and convert the reflected light into an electrical signal. Due to the uniqueness of the fingerprint characteristic of a finger of a different user, the light reflected by the finger of the different user will have a different characteristic. Accordingly, an electrical signal acquired by the light-sensitive sensing element is also different. These electrical signals can be received and analyzed by a processor for a fingerprint identification, thereby identifying the fingerprint.

An array substrate according to embodiments of the present disclosure includes a base substrate, a plurality of sensing elements and a plurality of switching devices. The plurality of sensing elements are disposed on a first side of the base substrate and each configured to convert at least one of a light signal and an acoustic wave signal into an electrical signal; and the plurality of switching devices are disposed on a second side of the base substrate opposite to the first side. The plurality of switching devices include a plurality of first switching elements, and each of the plurality of first switching elements is electrically connected to one of the plurality of sensing elements to transmit the electrical signal.

It can be appreciated that the sensing element includes, but not limited to, a photoelectric conversion element (for example, a photosensitive sensor) or an acoustoelectric conversion element (for example, an acoustic sensor), the first switching element may transmit the electrical signal generated by the sensing element, and these electrical signals may be provided to a processor or a controller to be calculated and analyzed, thereby identifying the fingerprint. Since the sensing elements and the switching devices are all attached to the base substrate as parts of a structure of the array substrate, a fingerprint identification function can be integrated in a display apparatus that is embodied based on this array substrate, thereby achieving a true fusion of the fingerprint identification function and the display apparatus. Furthermore, the sensing element and the switching device are manufactured on different sides of the base substrate, respectively. In this way, an interference between a manufacturing process of the switching device and a manufacturing process of the sensing element can be reduced or avoided.

The array substrate according to the present disclosure will be described below by way of specific examples. Detailed descriptions of known functions and components are omitted for the sake of brevity. When any one component appears in a plurality of figures, the component is denoted by the same reference numeral in each figure.

FIG. 1 is a schematic partial diagram (sectional view) of an array substrate 100 according to an embodiment of the present disclosure. The array substrate 100 may be an array substrate of a liquid crystal display apparatus having a backlight source, or may also be an array substrate of an active light-emitting display apparatus (for example, an electroluminescent organic light-emitting diode display apparatus) without backlight source. There is no limitation on where the array substrate 100 is applied in the present embodiment. As shown in FIG. 1, the array substrate 100 includes a base substrate 101, a plurality of sensing elements 102 disposed on a first side S1 of the base substrate, and a plurality of switching devices disposed on a second side S2 of the base substrate. Each of the plurality of sensing elements 102 is configured to convert at least one of a light signal and an acoustic wave signal into an electrical signal. The plurality of switching devices include first switching elements 104, and each of the first switching elements 104 is electrically connected to a corresponding one of the plurality of sensing elements 102 to transmit the electrical signal generated by the one of the plurality of sensing elements 102. FIG. 1 shows schematically shows an electric connection between the first switching element 104 and the sensing element 102 by a line. However, the electric connection can be embodied in any manner that is achievable by those skilled in the art, and there is no limitation on the electric connection in the present disclosure.

The base substrate 101 may be a glass substrate, a quartz substrate, a plastic substrate, or a substrate of any other suitable material. There is no specific limitation on a material of the base substrate 101 in the present disclosure. For example, the base substrate 101 may be a transparent substrate. In an example, the base substrate 101 may also be a flexible base substrate. The switching devices and the first switching elements 104 each include, but not limited to, switching elements such as a thin film transistor and the field-effect transistor. There is no specific limitation on a specific type of the switching device in the present disclosure.

Figure 2:
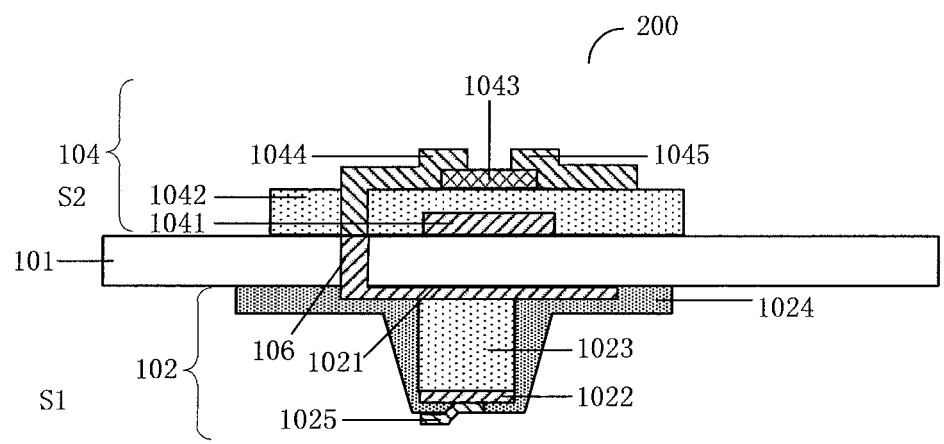
FIG. 2 is a schematic partial sectional view of an array substrate according to an embodiment of the present disclosure.

FIG. 2 schematically shows an example of structures of a sensing element and a switching device in an array substrate 200 according to an embodiment of the present disclosure. As shown in FIG. 2, in the array substrate 200, the sensing element 102 is disposed on the first side S1 of the base substrate 101. The sensing element 102 includes a first electrode 1021, a second electrode 1022, and a sensing layer 1023 disposed between the first electrode 1021 and the second electrode 1022. The first electrode 1021 is electrically connected to the first switching element 104, and the second electrode 1022 is configured to receive a reference electric potential. In an example, the first electrode 1021 and the second electrode 1022 are made of a transparent conductive material. An example of the transparent conductive material includes, but not limited to, an indium tin oxide (ITO). As described above, each of the plurality of sensing elements 102 is configured to convert at least one of a light signal and an acoustic wave signal into an electrical signal. Accordingly, a material of the sensing layer 1023 may include a light sensitive material that can receive a light signal to generate an electrical signal, or the material of the sensing layer 1023 includes a sound sensitive material such as indium zinc oxide (IZO) to convert an acoustic wave signal into an electrical signal.

When the sensing layer 1023 includes the light sensitive material, the sensing element 102 is actually a photoelectric conversion element. In a fingerprint identification stage, a light (which, for example, originates from a backlight source of a display apparatus in which the array substrate is located) reflected by a finger enters the sensing element 102, and the sensing layer 1023 can receive the reflected light and generate an electrical signal based on the reflected light. Since a fingerprint of a finger of each person has a unique texture feature, lights reflected from fingers of different users have different characteristics, so that the sensing element 102 also generates different electrical signals in response to the different reflected lights. The electrical signal generated by the sensing element 102 may be transmitted to a processor or a controller through the first switching element 104, so that the electrical signal is calculated and analyzed, thereby acquiring fingerprint information. Alternatively, in an example in which the sensing layer 1023 includes the sound sensitive material, the sensing element 102 actually converts an acoustic wave signal into an electrical signal. For example, the sensing layer 1023 may be an ultrasonic sensor. In this case, an ultrasonic wave generator may be disposed in a display apparatus to which the array substrate is applied, to transmit an ultrasonic wave to a finger of a user when the finger of the user approaches or touches the display apparatus. A reflected sound wave is formed when the ultrasonic wave meets the finger of the user, and the sensing layer including the sound sensitive material can receive the reflected sound wave to generate an electrical signal. Likewise, due to the uniqueness of the individual fingerprint characteristic of a finger of a user, sound waves reflected from fingers of different users have different frequencies. Thereby, the sensing element can generate different electrical signals based on the sound waves reflected from the fingers of the different users. Similarly, the fingerprint information of a user can be analyzed and identified by means of the electrical signal.

In the example shown in FIG. 2, the sensing element 102 may further include a dielectric layer 1024, a connecting wire 1025, and the like. The dielectric layer 1024 may cover the first electrode 1021, the sensing layer 1023, and the second electrode 1022 of the sensing element 102 to protect them. The second electrode 1022 is connected to the reference electric potential, for example through the connecting wire 1025. The first electrode 1021 of the sensing element 102 is connected to the first switching element 104 through the via hole 106 located in the base substrate. In the present example, the first switching element 104 is a thin film transistor including: a gate electrode 1041, a gate insulating layer 1042, an active layer 1043, a source electrode 1044, and a drain electrode 1045.

The example of FIG. 2 shows only a single sensing element 102 and a first switching element 104 connected to the single sensing element 102 through a via hole 106. However, it can be appreciated that in practice, the array substrate may include a plurality of sensing elements 102 and a plurality of first switching elements 104, the array substrate is formed with a plurality of via holes 106 accordingly, and the first electrode of each of the plurality of sensing elements is electrically connected to a corresponding one of the plurality of first switching elements through a corresponding one of the plurality of via holes 106. In some embodiments, a diameter of each of the plurality of via holes and a spacing between two adjacent ones of the plurality of via holes each are not greater than an interline spacing of a fingerprint of a finger. A fingerprint image includes ridge lines and valley lines, and the interline spacing refers to a spacing between one of the ridge lines and one of the valley lines which is adjacent to the one of the ridge lines. For example, generally the interline spacing of a fingerprint of a finger of a normal person is about 100 μm-300 μm, the diameter of each of the plurality of via holes 106 is about 10 μm-100 μm, and the spacing between two adjacent ones of the plurality of via holes is about 100 μm-200 μm, thereby facilitating an achievement of a high fingerprint identification accuracy.

Figure 3:
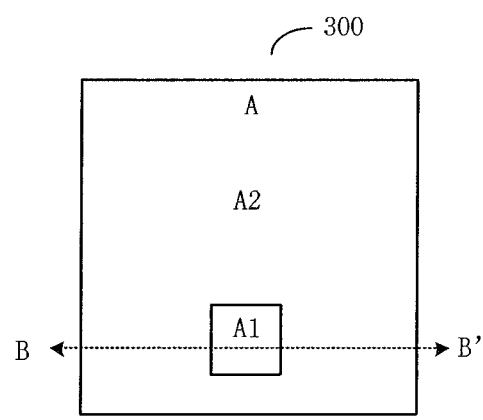
FIG. 3 is a schematic plan view of an array substrate according to an embodiment of the present disclosure.

An array substrate according to an embodiment of the present disclosure includes a display area, and the display area includes: a first region within which the plurality of sensing elements and the plurality of first switching elements are located; and a second region around the first region. FIG. 3 schematically shows the display area A of the array substrate, the first region A1, and the second region A2 around the first region A1. In the present example, the first region A1 may be used as a fingerprint identification region. When a finger of a user approaches or touches the first region A1, a fingerprint of the finger of the user can be identified.

Figure 4:
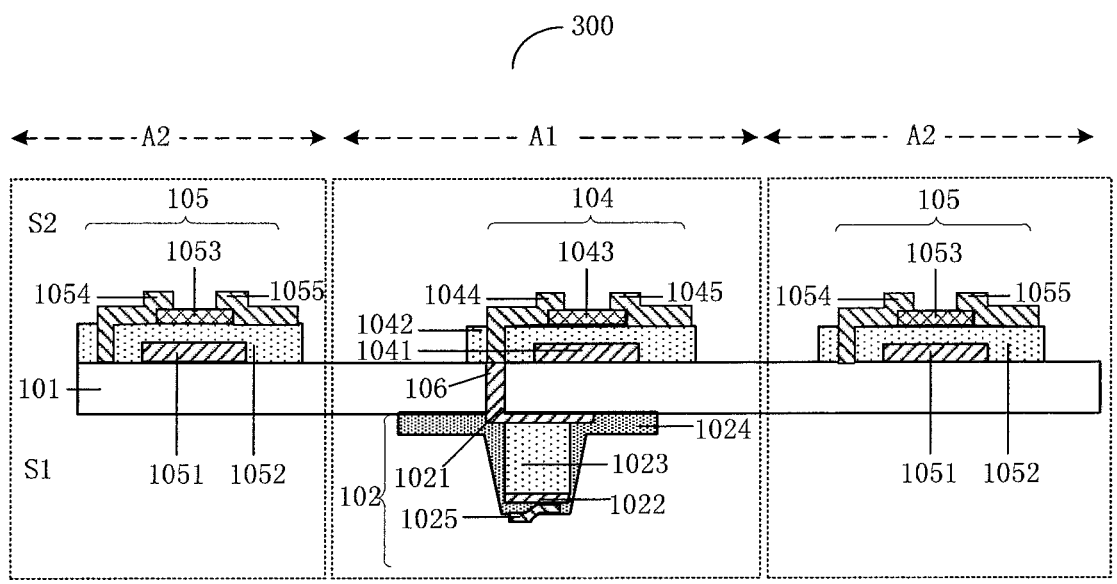
FIG. 4 is a schematic sectional view taken along the line B-B' in FIG. 3.

FIG. 4 is a schematic structural sectional view taken along the line B-B' in FIG. 3; As shown in FIG. 4, the plurality of switching devices disposed on the second side of the base substrate further include second switching elements 105. Each of the first switching element 104 and the second switching element 105 may include a thin film transistor. The first switching element 104 includes: a gate electrode 1041, a gate insulating layer 1042, an active layer 1043, a source electrode 1044, a drain electrode 1045, and the like. The second switching element 105 includes: a gate electrode 1051, a gate insulating layer 1052, an active layer 1053, a source electrode 1054, a drain electrode 1055, and the like. The first electrode 1021 of each of the plurality of sensing elements is electrically connected to a source electrode 1044 or a drain electrode 1045 of a corresponding one of the plurality of first switching elements 104. Referring to FIGS. 3 and 4, the plurality of sensing elements 102 and the plurality of first switching elements 104 are disposed within the first region A1, and the second switching elements 105 are disposed within the second region A2. Since the sensing elements 102 are attached to the base substrate 101 and are disposed within the display area A of the array substrate 300, it is unnecessary to additionally dispose a sensor for a fingerprint identification on another component (for example, a frame or a housing) of a display apparatus to which the array substrate is applied, thereby facilitating a narrow-frame design or a full-screen display of the display apparatus.

In the present embodiment, a gate electrode of each of the plurality of first switching elements 104 and the second switching elements 105 is configured to receive a first control signal to drive a pixel in the display area in a first period of time, and the gate electrode of each of the plurality of first switching elements 104 is further configured to receive a second control signal to transmit the electrical signal in a second period of time. In other words, in the first period of time, the plurality of first switching elements 104 and the second switching elements 105 are turned on or off in response to the first control signal to drive the pixels in the display area A for displaying an image. In the second period of time, the plurality of first switching elements 104 are turned on or off in response to the second control signal to transmit the electrical signals generated by the sensing elements to the controller or the processor (not shown), so that the electrical signals are calculated and analyzed, thereby achieving a fingerprint identification function. In some embodiments, in the second period of time, the second switching elements in the second region A2 may be controlled to be in an off state, or an application of the first control signal to the second switching elements may be stopped to reduce an energy consumption of the display apparatus. The first control signal is also referred to as an image display scan signal for displaying an image, and the second control signal is also referred to as a fingerprint identification scan signal for identifying a fingerprint.

Based on the embodiment shown in FIG. 4, the first switching elements 104 are actually provided to achieve two functions. In the first period of time (for example, a displaying stage), the first switching elements 104 and the second switching elements 105 act in response to the first control signal to achieve a normal image display. In the second period of time (for example, a fingerprint identification stage), the first switching elements act in response to the second control signal to transmit the electrical signals which are generated by the sensing elements for identifying a fingerprint. Therefore, the first switching element 104 may serve as a pixel switch for displaying an image in the first period of time, and may serve as a signal transmission switch for transmitting the electrical signal of the sensing elements in the second period of time. Therefore, in the embodiment, it is avoided to provide a dedicated fingerprint identification signal transmission switch configured to transmit a fingerprint identification signal for the array substrate or the display apparatus, thereby greatly reducing the number of the switching devices used in the array substrate and the display apparatus having a fingerprint recognition function, simplifying a circuit structure of the array substrate, and effectively decreasing a thickness of the array substrate and a thickness of the display apparatus.

In the example shown in FIG. 4, the first electrode 1021 of each of the plurality of sensing elements 102 is electrically connected to a source electrode 1044 of a corresponding one of the plurality of first switching elements 104. Alternatively, the first electrode 1021 of each of the plurality of sensing elements 102 may also be electrically connected to a drain electrode 1045 of a corresponding one of the plurality of first switching elements 104. There is no limitation on a specific manner of the electrical connection of the sensing element 102 to the first switching element 104 in the present disclosure as long as the first switching element 104 can transmit the electrical signal of the sensing element 102.

The inventors of the present application have realized that in a typical display apparatus, light emitted by the light source is not effectively utilized. For example, in a liquid crystal display apparatus, in an optical path from a backlight source to a light exit face of the display apparatus, a structure that blocks a propagation of light from the backlight source is provided; and in an organic light-emitting diode display apparatus, light emitted towards a back face, opposite to a light exit face, of the display apparatus is also not effectively utilized. Therefore, according to another embodiment of the present disclosure, the array substrate further includes a metal lead electrically connected to the first electrodes of the plurality of sensing elements and configured to be electrically connected to an energy storage element that is independent of the array substrate. The energy storage element includes, but not limited to, a rechargeable battery in the display apparatus to which the array substrate is applied. Thereby, the sensing elements can receive a portion of the light that is not effectively utilized and convert it into electrical signals. The electrical signals can be transmitted to the energy storage element, through the metal lead, to be stored, thereby increasing a light utilization efficiency of the display apparatus. This will be further described below by way of examples.

Figure 5:
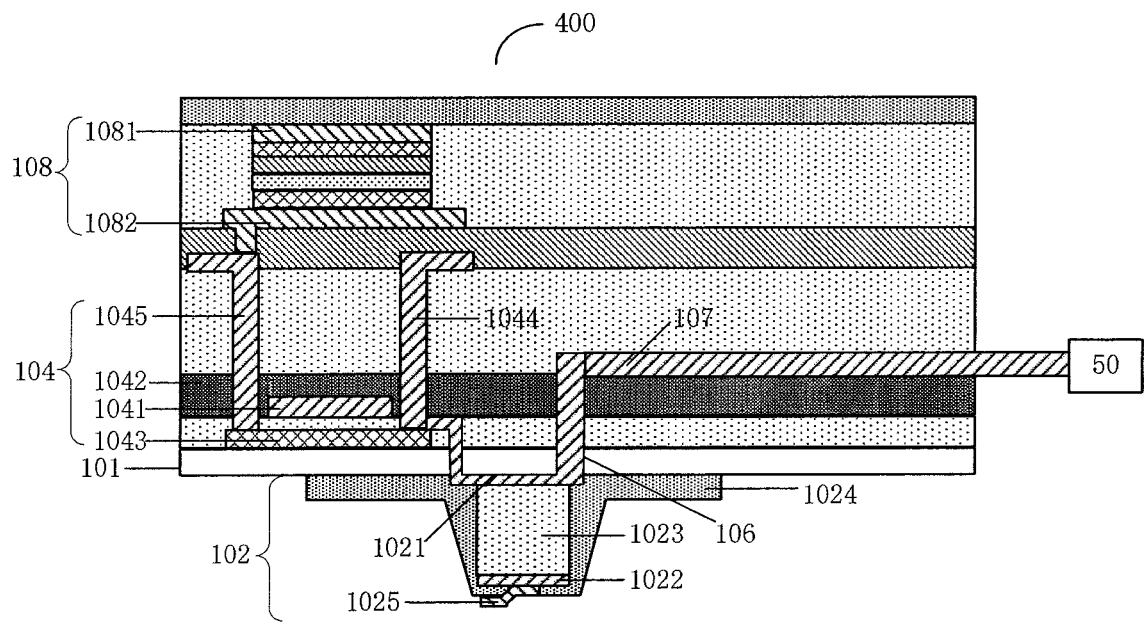
FIG. 5 is a schematic partial sectional view of an array substrate according to another embodiment of the present disclosure.

FIG. 5 is a schematic structural partial sectional view of an array substrate 400 according to another embodiment of the present disclosure. The array substrate 400 includes the sensing element 102 described in the above embodiments. The sensing element 102 is embodied as a photoelectric sensor in the present embodiment. In the present embodiment, the array substrate 400 is an array substrate for an electroluminescent organic light-emitting diode (for example, OLED) display apparatus.

As shown in FIG. 5, the array substrate 400 includes an electroluminescent organic light-emitting element 108 disposed on the second side S2 of the base substrate 101 and electrically connected to the first switching element 104. The electroluminescent organic light-emitting element 108 includes a cathode 1081, an anode 1082, an organic light-emitting layer between the cathode 1081 and the anode 1082, and the like. In the present example, the anode 1082 of the electroluminescent organic light-emitting element 108 is electrically connected to a drain electrode 1045 of the first switching element 104. Alternatively, the anode 1082 of the electroluminescent organic light-emitting element 108 may be electrically connected to a source electrode 1044 of the first switching element 104.

In the example shown in FIG. 5, an orthogonal projection of each of the sensing layers 1023 on the base substrate 101 does not overlap an orthogonal projection of a non-transparent region of a corresponding one of the first switching elements 104 on the base substrate 101 and an orthogonal projection of a non-transparent region of a corresponding one of the electroluminescent organic light-emitting elements 108 on the base substrate 101. As a result, the sensing layer 1023 efficiently may receive light propagating downwards or laterally from the electroluminescent organic light-emitting element 108, thereby improving a utilization ratio of light emitted from the electroluminescent organic light-emitting element 108. In other words, the orthogonal projection of each of the sensing layers 1023 on the base substrate 101 is located outside the orthogonal projection of the non-transparent region of the corresponding one of the first switching elements 104 on the base substrate 101 and the orthogonal projection of the non-transparent region of the corresponding one of the electroluminescent organic light-emitting elements 108 on the base substrate 101. The non-transparent regions of the first switching element 104 and the electroluminescent organic light-emitting element 108 mentioned herein mean structures, having a light blocking property, of the first switching element 104 and the electroluminescent organic light-emitting element 108, for example the gate electrode 1041, the source electrode 1044, and the drain electrode 1045 of the first switching element, the cathode 1081 or the anode 1082 of the electroluminescent organic light-emitting element 108, and the like. As shown in FIG. 5, the array substrate 400 further includes a metal lead 107 electrically connected to the first electrodes 1021 of the plurality of sensing elements 102. The metal lead 107 may be electrically connected to an energy storage element 50 (for example a rechargeable battery) that is independent of the array substrate 400. According to an example of the present disclosure, the array substrate 400 further includes a metal lead 107 electrically connected to the first electrodes 1021 of the plurality of sensing elements 102, the sensing layers 1023 each include a light sensitive material and are configured to convert a received light into an electrical signal in a state where the sensing elements 102 do not identify a fingerprint, and the metal lead 107 is configured to be electrically connected to an energy storage element that is independent of the array substrate 400, so that the electrical signal is transmitted to the energy storage element. For example, the electrical signal is transmitted to a rechargeable battery to charge the rechargeable battery.

It can be appreciated that the above embodied principle of improving of the light utilization ratio is not only applicable to an electroluminescent organic light-emitting diode display apparatus, but also to a liquid crystal display apparatus including a backlight source. In the liquid crystal display apparatus, generally the backlight source is disposed on a side of the base substrate facing away from the thin film transistors. Generally, light incident on a light blocking metal layer such as a gate electrode, a source electrode, and a drain electrode of a thin film transistor cannot be effectively utilized, resulting in waste of energy.

Referring to FIG. 2 again, according to an embodiment of the present disclosure, the array substrate 200 is an array substrate for a liquid crystal display apparatus, and an orthogonal projection of the sensing layer 1023 of each of the sensing elements 102 on the base substrate 101 coincides at least partly with an orthogonal projection of a corresponding one of the plurality of first switching elements 104 on the base substrate 101. When the display apparatus is in operation, the backlight source independent of the array substrate 200 typically emits light from below the array substrate 200. As the orthogonal projection of the sensing layer 1023 of each of the sensing elements 102 on the base substrate 101 coincides at least partly with the orthogonal projection of the corresponding one of the plurality of first switching elements 104 on the base substrate 101, at least a part of the backlight which otherwise would be blocked by the first switching element 104 can enter the sensing element and be converted into electrical energy to be stored and utilized. On the other hand, this can also reduce an influence of the sensing element 102 on a propagation of the backlight required to display an image. In some embodiments, the orthogonal projection of the sensing layer 1023 of each of the sensing elements 102 on the base substrate 101 is located within the orthogonal projection of the corresponding one of the plurality of first switching elements 104 on the base substrate 101. In this way, the influence of the sensing element 102 on the propagation of the backlight required to display the image can be reduced to the maximum extent.

Another embodiment of the present disclosure provides a display apparatus including the array substrates described in any one of the above embodiments. For example, the display apparatus may include any products or parts having a displaying function, such as a mobile phone, a tablet computer, a notebook computer, a camera, and a navigator.

Figure 6:
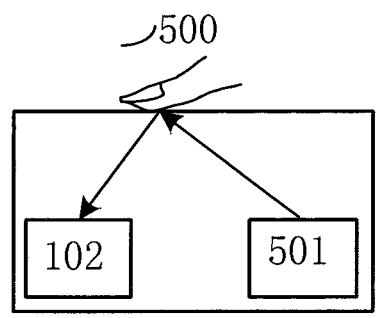
FIG. 6 is a schematic diagram showing a structure of a portion of a display apparatus according to an embodiment of the present disclosure.

The array substrate of the display apparatus includes the sensing elements. In an embodiment, each of the plurality of sensing elements is an acoustic sensor configured to convert the acoustic wave signal into the electrical signal. In this case, the display apparatus may further include an acoustic wave generator configured to generate an acoustic wave. FIG. 6 schematically shows a structure of a portion of an exemplary display apparatus 500. As shown in FIG. 6, the display apparatus 500 includes a sensing element 102 and an acoustic wave generator 501. The sensing element 102 is an acoustic sensor arranged on the array substrate. The acoustic wave generator 501 may be disposed on any other appropriate structure of the display apparatus. For example, the acoustic wave generator 501 may be attached to any other appropriate component of the display apparatus such as a back plate, a frame or a housing. The acoustic wave generator 501 may be, for example, an ultrasonic wave generator. When a finger of a user touches or approaches a surface of the display apparatus, the acoustic wave generator 501 can transmit an acoustic wave signal towards the finger. A reflected sound wave is generated when the sound wave meets the finger of the user. The acoustic sensor 102 can receive the reflected sound wave to generate an electrical signal. Due to the uniqueness of the individual fingerprint characteristic of a finger of a user, sound waves reflected from fingers of different users have different frequencies. Thereby, the sensing element can generate different electrical signals based on the sound waves reflected from the fingers of the different users. Therefore, the fingerprint information of a user can be analyzed and identified based on the electrical signal.

In another embodiment, the display apparatus further includes a rechargeable battery, and the plurality of sensing elements 102 are electrically connected to the rechargeable battery. As described above, the sensing elements can receive the portion, which is not effectively utilized, of the light in the display apparatus and convert it into the electrical signal, and the plurality of sensing elements are electrically connected to the rechargeable battery. Therefore, when the display apparatus is in operation, the electrical signals may be transmitted to the rechargeable battery, that is, the rechargeable battery is charged, in a state where the sensing elements do not identify a fingerprint. In this way, a light utilization efficiency of the display apparatus can be increased.

Based on the same inventive concept, a further embodiment of the present disclosure provides a method of manufacturing an array substrate. The method may be used to manufacture the array substrate described in the above embodiments. The method includes the following steps: providing a base substrate; forming, on a first side of the base substrate, a plurality of sensing elements each configured to convert at least one of a light signal and an acoustic wave signal into an electrical signal; and forming a plurality of switching devices on a second side of the base substrate opposite to the first side. The plurality of switching devices include a plurality of first switching elements, and each of the plurality of first switching elements is electrically connected to one of the plurality of sensing elements to transmit the electrical signal.

In some embodiments, each of the plurality of sensing elements includes a first electrode, a second electrode, and a sensing layer located between the first electrode and the second electrode, and the method further includes: forming a plurality of via holes in the base substrate. The first electrode of each of the plurality of sensing elements is electrically connected to a corresponding one of the plurality of first switching elements through a corresponding one of the plurality of via holes. An example of a method of manufacturing an array substrate will be schematically explained below with reference to FIGS. 7A to 7G.

Figure 7A:
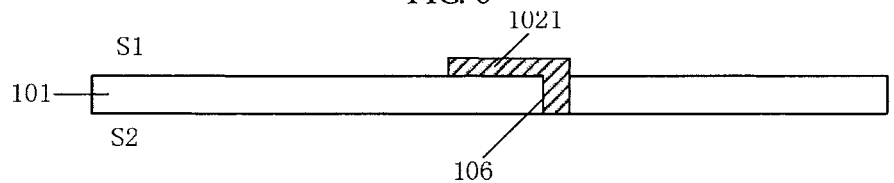
FIGS. 7A-7G schematically show steps of a method of manufacturing an array substrate according to another embodiment of the present disclosure.

As shown in FIG. 7A, firstly, a base substrate 101 is provided. The base substrate 101 may be, for example, a glass substrate, a quartz substrate, a plastic substrate, or a substrate of any other suitable material. In an example, the base substrate 101 may also be a flexible base substrate. As shown in FIG. 7A, a plurality of via holes (only one via hole 106 is shown in FIG. 7A) are formed in the base substrate 101. A diameter of each of the plurality of via holes 106 and a spacing between two adjacent ones of the plurality of via holes each are not greater than an interline spacing of a fingerprint of a finger. In an example, the diameter of each of the plurality of via holes 106 is about 10 µm-100 µm, and the spacing between two adjacent ones of the plurality of via holes is about 100 µm-200 µm. Furthermore, a metal film may be deposited on a first side S1 of the base substrate 101 formed with the plurality of via holes 106, for example by a method such as a chemical vapor deposition or a physical vapor deposition, and may be patterned by a photolithographic process, so that a first electrode 1021 is formed on the first side S1 of the base substrate 101. The via holes 106 may be filled with the material of which the first electrode 1021 is made.

Figure 7B:
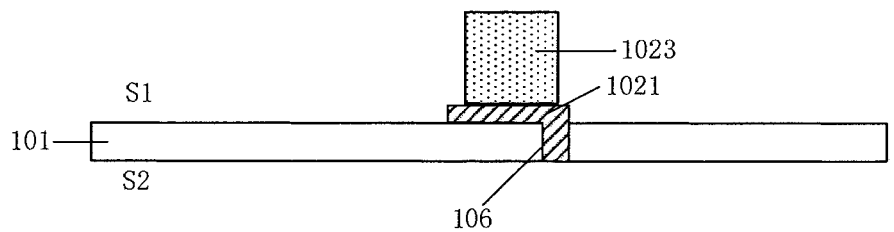

As shown in FIG. 7B, a sensing layer film is deposited on the base substrate 101 which is formed with the first electrode 1021 and is patterned to form a sensing layer 1023. The sensing layer 1023 includes a light sensitive material, such as an amorphous silicon having a relatively high hydrogen content. Alternatively, the sensing layer includes a sound sensitive material. In the present embodiment, since the switching device for transmitting the electrical signal generated by the sensing element has not yet been manufactured at the time of manufacturing the sensing layer, the process involved in manufacturing the sensing layer 1023 does not adversely affect the subsequent manufacturing process of the switching device, thereby avoiding an influence on the performance of the switching device.

Figure 7C:
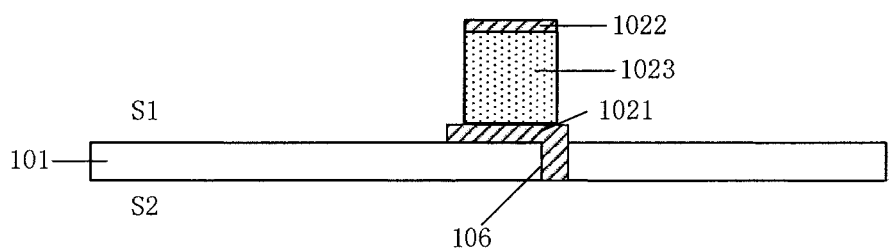

Next, as shown in FIG. 7C, a second electrode 1022 is formed on the base substrate 101 formed with the sensing layer 1023. A material of which the first electrode 1021 and the second electrode 1022 are made includes a transparent conductive material, for example, any appropriate material such as indium tin oxide (ITO) and tin oxide (ZnO).

Figure 7D:
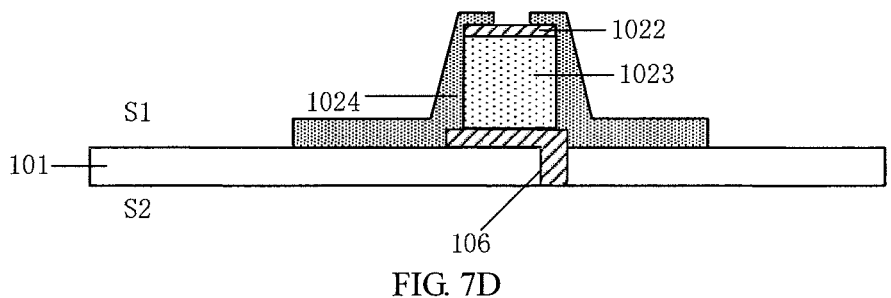
Figure 7E:
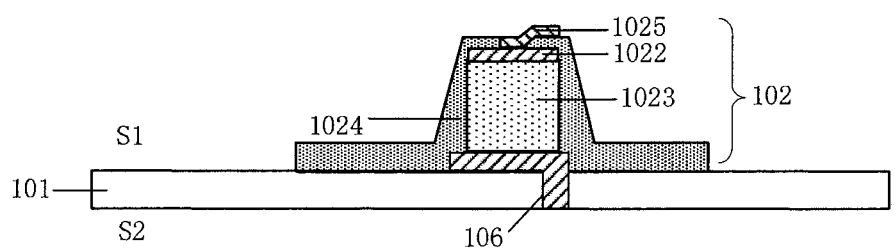

In some embodiments, as shown in FIGS. 7D and 7E, a dielectric layer 1024 and a connecting wire 1025 are formed on the first side S1 of the base substrate 101. The dielectric layer 1024 substantially covers the first electrodes, the second electrodes, and the sensing layers to isolate and protect the first electrodes, the second electrodes, and the sensing layers of the sensing elements. The second electrode 1022 may be connected to the reference electric potential through the connecting wire 1025.

Figure 7F:
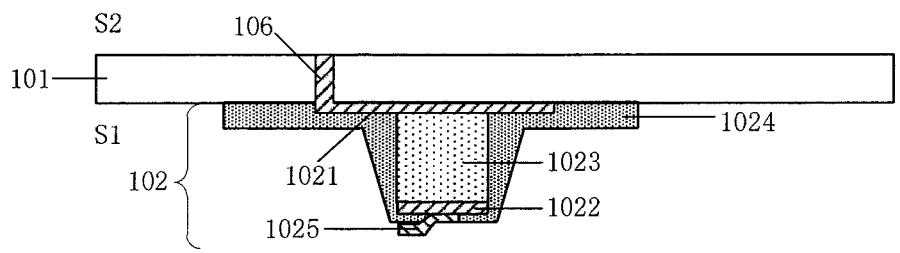

In some embodiments, as shown in FIG. 7F, after the sensing element 102 is formed on the first side S1 of the base substrate 101, the base substrate 101 formed with the sensing element 102 is inverted to manufacture the switching device configured to transmit the electrical signal on the second side S2 of the base substrate.

Figure 7G:
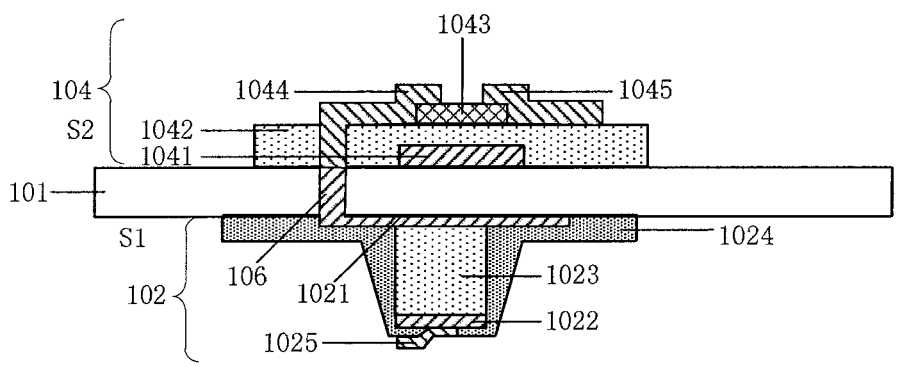

As shown in FIG. 7G, a first switching element 104 is formed on the second side S2 of the base substrate 101. The first switching element 104 may be, for example, a thin film transistor. A conventional process of manufacturing a thin film transistor may be referred to for a process of manufacturing the first switching element 104, and a process of manufacturing the first switching element is no longer described herein for the sake of brevity. The formed first switching element 104 and sensing element 102 may be located, for example, within the display area of the array substrate.

With the method of manufacturing the array substrate according to the present embodiment, the sensing element 102 and the switching device for transmitting the electrical signal generated by the sensing element are manufactured on the opposite sides of the base substrate 101, respectively. For example, in some embodiments, the sensing element 102 is first manufactured on the first side of the base substrate, and then the first switching element 104 is manufactured on the second side of the base substrate. In this case, on one hand, since the first switching element 104 is not yet formed when the sensing element is manufactured on the first side of the base substrate, complex process conditions required to manufacture the sensing element 102 do not affect the first switching element 104. On the other hand, an etching process involved in manufacturing the first switching element 104 on the second side of the base substrate does not adversely affect the sensing element that has been formed on the first side of the base substrate, either.

The above contents are only some exemplary embodiments of the present disclosure. However, the protection scope of the present application is not limited thereto. Changes or substitutions that can be easily conceived by any person skilled in the art within the technical scope disclosed in the present disclosure should be contained within the protection scope of the present application. The embodiments of the present disclosure and the features in the embodiments of the present disclosure may be combined with one another to obtain new embodiments unless they conflict. Therefore, the protection scope of the present application should be defined by the scope of the claims.

What is claimed is:

1. An array substrate comprising:
a base substrate;
a plurality of sensing elements disposed on a first side of the base substrate and each configured to convert at least one of a light signal and an acoustic wave signal into an electrical signal; and
a plurality of switching devices disposed on a second side of the base substrate opposite to the first side,
wherein the plurality of switching devices comprise a plurality of first switching elements, and each of the plurality of first switching elements is electrically connected to a corresponding one of the plurality of sensing elements to transmit the electrical signal.

2. The array substrate of claim 1, wherein each of the plurality of sensing elements comprises a first electrode electrically connected to a corresponding one of the plurality of first switching elements, a second electrode configured to receive a reference electric potential, and a sensing layer disposed between the first electrode and the second electrode.

3. The array substrate of claim 2, wherein the base substrate comprises a plurality of via holes, the first electrode of each of the plurality of sensing elements is electrically connected to the corresponding one of the plurality of first switching elements through a corresponding one of the plurality of via holes, and wherein a diameter of each of the plurality of via holes and a spacing between two adjacent ones of the plurality of via holes each are not greater than an interline spacing of a fingerprint of a finger.

4. The array substrate of claim 2, wherein the array substrate comprises a display area, and the display area comprises: a first region within which the plurality of sensing elements and the plurality of first switching elements are located; and a second region around the first region.

5. The array substrate of claim 4, wherein the plurality of switching devices further comprise second switching elements located in the second region, and the plurality of first switching elements and the second switching elements each comprise a thin film transistor, and wherein the first electrode of each of the plurality of sensing elements is electrically connected to a source electrode or a drain electrode of one of the plurality of first switching elements, and wherein a gate electrode of each of the plurality of first switching elements and the second switching elements is configured to receive a first control signal to drive a pixel in the display area in a first period of time, and the gate electrode of each of the plurality of first switching elements is further configured to receive a second control signal to transmit the electrical signal in a second period of time.

6. The array substrate of claim 2, further comprising:
a metal lead electrically connected to the first electrodes of the plurality of sensing elements and configured to be electrically connected to an energy storage element that is independent of the array substrate.

7. The array substrate of claim 6, further comprising:
electroluminescent organic light-emitting elements located on the second side of the base substrate and electrically connected to the plurality of switching devices, respectively,
wherein an orthogonal projection of each of the sensing layers on the base substrate does not overlap an orthogonal projection of a non-transparent region of a corresponding one of the first switching elements on the base substrate and an orthogonal projection of a non-transparent region of a corresponding one of the electroluminescent organic light-emitting elements on the base substrate.

8. The array substrate of claim 6, wherein an orthogonal projection of each of the sensing layers on the base substrate coincides at least partly with an orthogonal projection of a corresponding one of the plurality of first switching elements on the base substrate.

9. The array substrate of claim 2, wherein the sensing layer comprises a light sensitive material or a sound sensitive material.

10. The array substrate of claim 2, wherein each of the plurality of sensing elements comprises a dielectric layer covering the first electrode, the second electrode, and the sensing layer of the each of the plurality of sensing elements.

11. The array substrate of claim 2, further comprising:
a metal lead electrically connected to the first electrodes of the plurality of sensing elements,
wherein the sensing layers each comprise a light sensitive material and are configured to convert a received light into an electrical signal in a state where the sensing elements do not identify a fingerprint, and the metal lead is configured to be electrically connected to an energy storage element that is independent of the array substrate, so that the electrical signal is transmitted to the energy storage element.

12. A display apparatus comprising the array substrate of claim 1.

13. The display apparatus of claim 12, wherein each of the plurality of sensing elements comprises an acoustic sensor configured to convert the acoustic wave signal into the electrical signal, and wherein the display apparatus further comprises an acoustic wave generator configured to generate an acoustic wave.

14. The display apparatus of claim 12, further comprising:
a rechargeable battery,
wherein the plurality of sensing elements are further electrically connected to the rechargeable battery.

15. The display apparatus of claim 12, further comprising:
a rechargeable battery,
wherein the array substrate further comprises a metal lead electrically connected to the first electrodes of the plurality of sensing elements, the sensing layers each comprise a light sensitive material and are configured to convert a received light into an electrical signal in a state where the sensing elements do not identify a fingerprint, and the metal lead is configured to be electrically connected to the rechargeable battery, so that the electrical signal is transmitted to the rechargeable battery.

16. A method of manufacturing an array substrate, the method comprising:
providing a base substrate;
forming, on a first side of the base substrate, a plurality of sensing elements each configured to convert at least one of a light signal and an acoustic wave signal into an electrical signal; and
forming a plurality of switching devices on a second side of the base substrate opposite to the first side,
wherein the plurality of switching devices comprise a plurality of first switching elements, and each of the plurality of first switching elements is electrically connected to a corresponding one of the plurality of sensing elements to transmit the electrical signal.

17. The method of claim 16, wherein each of the plurality of sensing elements comprises a first electrode, a second electrode, and a sensing layer located between the first electrode and the second electrode, and wherein the method further comprises:
forming a plurality of via holes in the base substrate, wherein the first electrode of each of the plurality of sensing elements is electrically connected to a corresponding one of the plurality of first switching elements through a corresponding one of the plurality of via holes.

18. The method of claim 17, further comprising:
forming a dielectric layer on a first side of the base substrate, wherein the dielectric layer covers the first electrodes, the second electrodes, and the sensing layers of the plurality of sensing elements.

19. The method of claim 17, wherein the array substrate comprises a display area, and the display area comprises: a first region within which the plurality of sensing elements and the plurality of first switching elements are located; and a second region around the first region.

20. The method of claim 19, wherein the plurality of switching devices further comprise second switching elements located in the second region, and the plurality of first switching elements and the second switching elements each comprise a thin film transistor, and wherein the first electrode of each of the plurality of sensing elements is electrically connected to a source electrode or a drain electrode of a corresponding one of the plurality of first switching elements, and
wherein a gate electrode of each of the plurality of first switching elements and the second switching elements is configured to receive a first control signal to drive a pixel in the display area in a first period of time, and the gate electrode of each of the plurality of first switching elements is further configured to receive a second control signal to transmit the electrical signal in a second period of time.

* * * * *